United States Patent [19]

Dornmair et al.

[11] Patent Number: 5,364,762
[45] Date of Patent: Nov. 15, 1994

[54] MAJOR HISTOCOMPATIBILITY COMPLEX (MHC) MOLECULES

[75] Inventors: Klaus Dornmair, Palo Alto; Harden M. McConnell, Stanford, both of Calif.

[73] Assignee: Board of Trustees of the Leland Stanford Junior University, Stanford, Calif.

[21] Appl. No.: 497,009

[22] Filed: Mar. 21, 1990

[51] Int. Cl.$^5$ .................. C07K 3/12; C07K 15/14; G01N 33/566

[52] U.S. Cl. .................... 435/7.24; 435/7.8; 436/501; 530/395; 530/402; 530/403; 530/412; 530/806

[58] Field of Search ............ 530/395, 403, 412, 806, 530/402; 435/7.24, 7.8; 436/501

[56] References Cited

U.S. PATENT DOCUMENTS

| | | | |
|---|---|---|---|
| 4,265,873 | 5/1981 | Sheey et al. | 435/7.24 |
| 4,400,376 | 8/1983 | Sanderson | 424/88 |
| 4,478,823 | 10/1984 | Sanderson | 424/88 |
| 4,861,589 | 8/1989 | Ju | 424/93 |

OTHER PUBLICATIONS

S. Bulls et al., *Cell,* 47, 1071–1077, 1986.
A. White et al., *Principles of Biochemistry,* Third Edition, McGraw-Hill, 1964, p. 137.
Grey, H. M., et al., Scientific American Nov., 1989:56–64.
Buus, S., et al., PNAS USA 83:3968–71 (1986).
Sadegh-Nasseri, S., et al., Nature 337:274–76 (1989).
Watts, T. H., et al., PNAS USA 83:9660–64 (1986).
Buus, S., et al., Science 235:1353–58 (1987).
Adorini, L., et al., Nature 334:623–25 (1988).
Demotz, S., et al., Nature 342:682–84 (1989).
Wallny, H. J., et al., Nature 343:275–78 (1990).
Jaenicke, R., Prog. Biophys. Molec. Biol. 49:117–237 (1987).
Harrison, S. C., et al., PNAS USA 82:4028–30 (1985).
Creighton, T. E., PNAS USA 85:5082–86 (1988).
Udgaonkar, J. B., et al., Nature 335:694–99 (1988).
Roder, H., et al., Nature 335:700–04 (1988).
Matouschek, A., et al., Nature 340:122–26 (1989).
Maher, P. A., et al., PNAS USA 83:9001–05 (1986).
Goldenberg, D. P., et al., Nature 338:127–32 (1989).
Matsumura, M., et al., Nature 342:291–93 (1989).
Rothenhäusler, B., et al., PNAS USA 87:352–54 (1990).
Buus, S., et al., Science 242:1045–47 (1988).
Brown, J. H., et al., Nature 332:845–50 (1988).
Kumar V., PNAS USA 87:1337–41 (1990).
Ozato, K., et al., J. Immunol. 126:317–21 (1981).
Braunstein, N. S., et al., PNAS USA 84:2921–25 (1987).

*Primary Examiner*—David Saunders
*Attorney, Agent, or Firm*—Townsend and Townsend Khourie and Crew

[57] ABSTRACT

Processes for increasing antigen binding capacity of a major histocompatibility complex (MHC) molecule or a chain thereof are described. Such processes comprise treating an antigen-bound MHC molecule or a chain thereof with an effective amount of an unfolding agent to release undesired antigen from the MHC molecule or chain and then treating the antigen-free MHC molecule or chain with an effective amount of a refolding agent to produce a functional MHC molecule or chain. Additionally, compositions of MHC molecules that are substantially free of undesired antigens or that have been bound with desired specific antigens, alone or in combination with pharmaceutically acceptable carriers and/or cytotoxic agents, are described. The present invention has utility for therapeutic administrations, drug screening, and diagnostics.

13 Claims, 5 Drawing Sheets

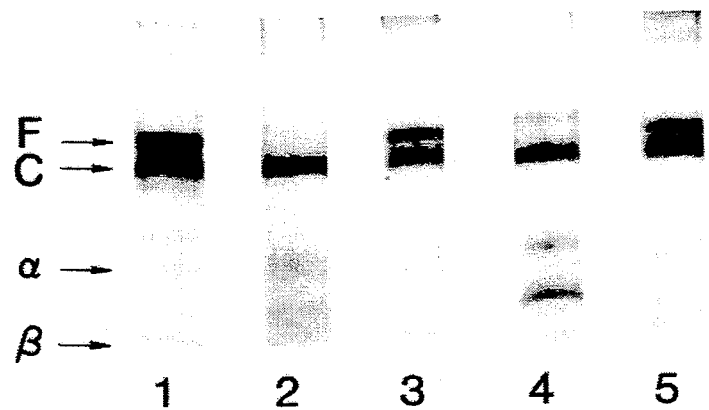
FIG. 1A
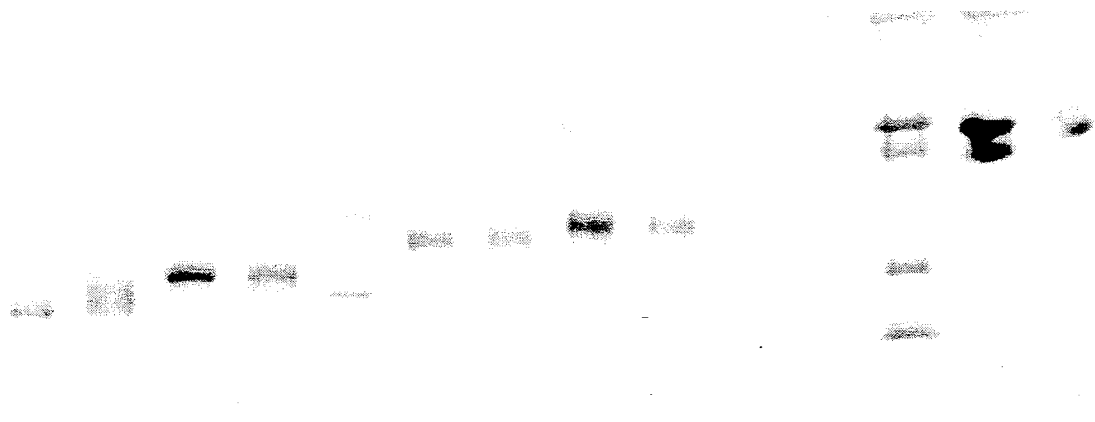
FIG. 2
FIG. 4
FIG. 3A

MAJOR HISTOCOMPATIBILITY COMPLEX (MHC) MOLECULES

This invention was made in part with United States government funding of a grant from the National Institutes of Health (NIH Grant No. 5R01 A1 13587-13); therefore, the government may have certain rights in this invention.

BACKGROUND OF THE INVENTION

1. Field of the Invention

The present invention relates generally to the field of immunology and, more particularly, to processes for increasing the antigen binding capacity of class I and class II MHC molecules and to compositions of MHC molecules that are substantially free of such antigens.

2. Brief Description of the Relevant Art

Major histocompatibility complex (MHC) molecules (glycoproteins) are expressed on cells of higher vertebrates and play a role in immune responses. These molecules were discovered as a result of tissue grafting experiments wherein it was shown that graft rejection is an immune response to foreign antigens on the surface of the grafted cells. In humans, MHC molecules are referred to as HLA (human-leukocyte-associated) antigens because they were first identified in leukocytes. In mice, they are designated H-2 antigens.

MHC molecules are divided into two groups, class I and class II, which differ structurally and functionally from each other. In general, the major function of MHC molecules is to bind antigenic peptides and to display them on the surface of cells. These peptides result from an antigen presenting cell (APC) processing an antigen into peptide fragments, which can be as short as 10 to 20 amino acids. Class I MHC molecules are expressed on almost all nucleated cells and are recognized by cytotoxic T lymphocytes, which then destroy the antigen-bearing cells. Class II MHC molecules are expressed primarily on cells involved in immune responses, such as T lymphocytes, B lymphocytes, macrophages, etc. Class II MHC molecules are recognized by helper T lymphocytes and induce proliferation of helper T lymphocytes and amplification of the immune response to the particular antigenic peptide that is displayed.

It is thought that an antigenic peptide first forms a complex with either a class I or class II MHC molecule, and this complex fits into a single recognition site in either a cytotoxic or helper T lymphocyte receptor, respectively. In addition to binding antigenic peptides, MHC molecules also can bind with autologous, or "self" peptides. If T lymphocytes then respond to cells presenting "self" peptides, a condition of autoimmunity results. For a general discussion of the function of MHC molecules, see Grey, H. M., et al., *Scientific American* November, 1989:56-64 (incorporated herein by reference).

MHC molecule-antigenic peptide complexes are extremely stable. It has been found that the rates of peptide binding (on-rate or association) and unbinding (off-rate or disassociation) are extremely slow, see Buus, S., et al., *Proc. Natl. Acad. Sci. USA* 83:3968-3971 (1986); Sadegh-Nasseri, S., et al *Nature* 338:274-276 (1989) (these publications are incorporated herein by reference), and that only a small fraction of isolated MHC molecules are able to bind to added peptides, even when such peptides are present in high concentration and for a long incubation time, see Watts, T. H., et al , *Proc. Natl. Acad. Sci. USA* 83:9660-9664 (1986); Buus, S., et al , *Science* 235:1353-1358 (1987); Adorini, L., et al., *Nature* 334:623-625 (1988) (these publications are incorporated herein by reference). This may be due to the fact that many of the MHC molecules still have peptides bound to them, even after the molecules have been isolated, see Demotz, S., et al., *Nature* 342:682-684 (1989); Wallny, H. J., et al., *Nature* 343:275-278 (1990) (these publications are incorporated herein by reference)

Difficulties in removing peptides bound to MHC molecules have stymied research on, for example, possible drug candidates to combat autoimmune conditions in the case where MHC molecules are bound to autologous proteins and also on screening methods for detecting certain antigenic peptides bound to the molecules. Although peptides have been removed from class II MHC molecules through inducing a change in pH, see Demotz, S., et al., *Nature* 342:682-684 (1989) (incorporated herein by reference), research has been centered on the peptides themselves and not the MHC molecules.

The unfolding and refolding of proteins, other than MHC glycoproteins, has been reported, see Jaenicke, R. *Prog. Biophys. molec. Biol.* 49:117-237 (1987) (incorporated herein by reference) for a review of such work, and the thermodynamic and kinetic mechanisms have been studied and folding intermediates have been characterized, see Harrison S. C., et al., *Proc. Natl Acad Sci USA* 83: 4028-4030 (1985); Creighton, T. E,, *Proc. Natl. Acad. Sci, USA* 83:5082-5086 (1988) Udgaonkar, J. B., et al., *Nature* 335:694-699 (1988) Roder, H., et al., *Nature* 335:700-704 (1988); and Mouschek, *Nature* 30:122-126 (1989) (all of these publications re incorporated herein by reference). Additionally, the role of disulfide bond formation has been investigated, see Maher, P. A., et al., *Proc. Natl. Acad. Sci. USA* 83:9001-9005 (1986); Goldenberg., D. P., et al., *Nature* 338:127-132 (1989); Matsumura, M., et al. *Nature* 342: 291-293 (1989) (all of these publications are incorporated herein by reference).

MHC molecules are the subject of Ju, U.S. Pat. No. 4,861,589; Sanderson, U.S. Pat. No. 4,478,823; Sanderson, U.S. Pat. No. 4,440,376; and Bach, et al., U.S. Pat. No. 4,265,873 (all of these patents are incorporated herein by reference).

SUMMARY OF THE INVENTION

The present invention comprises novel processes for increasing antigen binding capacity of a class I or class II major histocompatibility complex (MHC) molecule or chain thereof. An antigen-bound MHC molecule or chain thereof is treated with an effective amount of an unfolding agent, preferably a reducing agent whereby disulfide bonds of the MHC molecule are cleaved, to release the undesired antigen from the MHC molecule or chain thereof; the unfolding agent and released antigen are removed; and the antigen-free MHC molecule or chain thereof is treated with an effective amount of a refolding agent to produce a functional MHC molecule or chain thereof. A preferred unfolding agent is the reducing agent, dithiothreitol (DTT). A variety of agents can be used to refold the MHC molecule or chain thereof, thereby increasing the capacity of the MHC molecule or chain to bind antigens, including specific peptide fragments.

Additionally, the present invention comprises compositions comprised of MHC molecules or chains thereof that are substantially free of undesired antigens and that may contain specific peptide fragments, if desired. Such compositions can be combined with pharmaceutically acceptable carriers and cytotoxic agents for the treatment of, for example, autoimmune diseases or conditions. Compositions of MHC molecules or chains thereof that are substantially free of antigens can be labelled for assays. Processes to such uses are also described herein.

Thus, the processes and compositions of the present invention have utility in therapeutic administrations, drug screening, and diagnostics.

DESCRIPTION OF THE DRAWINGS

FIG. 1A is a silver-stained SDS gel, wherein:

Lane 1: $IA^d$ was incubated for 1 h at 37° C. in the presence of 100 μM FOva(323-339). The $\alpha/\beta$ heterodimeric floppy (F) and compact (C) conformations migrated with apparent molecular weights of 64 and 55 kD, and the separate $\alpha$- and $\beta$-chains with molecular weights of 33 and 27.5 kD, respectively.

Lane 2: $IA^d$ was reduced with 1 mM DTT for 1 h at 37° C. in the presence of 100 μM FOva(323-339).

Lane 3: The sample of Lane 2 was reoxidized by dialysis in an air-saturated buffer and subsequently incubated for 1 h at 37° C. with 100 μM FOva(3-23-339).

Lane 4: Identical to Lane 2, but 10 mM DTT were used for reduction instead of 1 mM DTT.

Lane 5: The sample of Lane 4 was reoxidized by dialysis in an air-saturated buffer and subsequently incubated for 1 h at 37° C. with 100 μM FOva(3-23-339).

Figures 1, 1B:
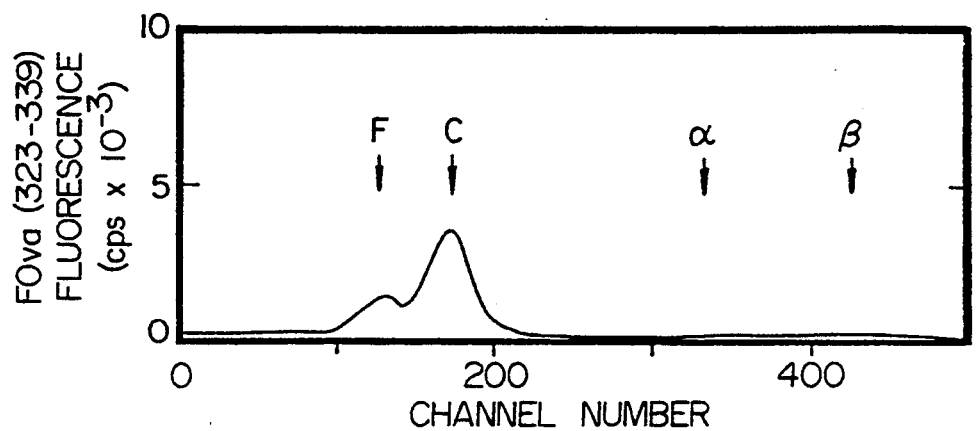
FIG. 1 demonstrates the effect of reduction with 1 mM and 10 mM dithiothreitol (DTT) and reoxidation on murine class II MHC molecules, $IA^d$.

FIG. 1B shows scans for fluorescent peptides bound to different conformations of $IA^d$. The samples of Lanes 1 to 5 in FIG. 1A were scanned for fluorescent peptides on a fluorescence microscope prior to fixation of the gels. It is evident that reduction (Lanes 2 and 4) leads to almost complete loss of peptides. Reoxidation (Lanes 3 and 5) restores peptide binding. The binding capacity of all conformations of $IA^d$ was significantly higher after reduction and reoxidation, compared to the untreated material (Lane 1).

Figures 1, 1B, 2:
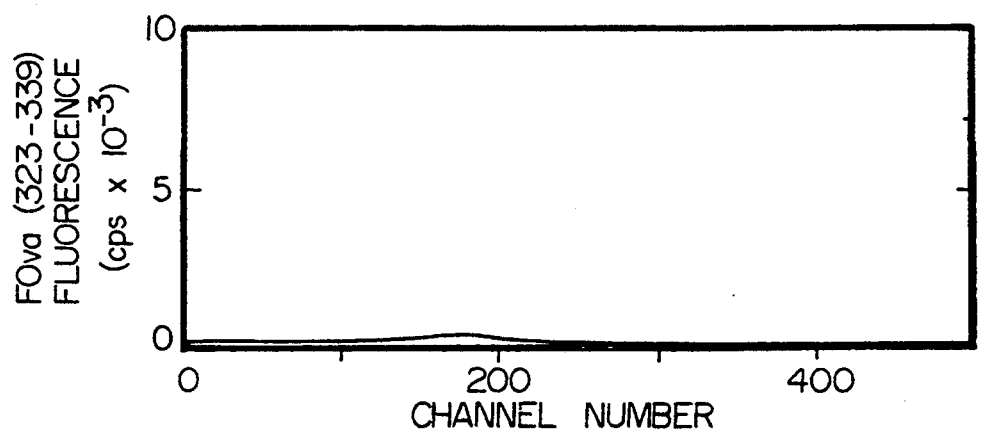

FIG. 2 demonstrates the unfolding of separate $\alpha$- and $\beta$-chains and shows silver-stained SDS gel for separate $\beta$-chains (Lanes 1-4) and $\alpha$-chains (Lanes 6-9) with and without reduction with varying concentrations of dithiothreitol (DTT), wherein:

Lane 1: The $\beta$-chain of $IA^d$ after electroelution from preparative SDS gels. The apparent molecular weight was $MW^{app}=27.5$ kD.

Lane 2: The $\beta$-chain was incubated for 1 h at 37° C. with 1 mM DTT. Three bands were visible with $MW^{app}=27.5$, 28.5 and 30 kD.

Lane 3: The $\beta$-chain was incubated for 1 h at 37° C. with 1 mM DTT. Only one band was seen migrating with $MW^{app}=30$ kD.

Lane 4: The $\beta$-chain was incubated for 30 min at 95° C. in the presence of 10 mM DTT. The apparent molecular weight was identical to that in Lane 3. However, aggregates migrating with $MW^{app}=60$ and 70 kD were detected.

Lane 5: Molecular weight standards. The proteins are: bovine serum albumin, hen egg albumin, carbonic anhydrase, and glyceraldehyde-3-phosphatedehydrogenase. Trypsin inhibitor and lysozyme are not shown.

Lane 6: The $\alpha$-chain of $IA^d$ after electroelution from preparative SDS gels. It migrates with $MW^{app}=33$ kD.

Lane 7: The $\alpha$-chain was incubated for 1 h at 37° C. with 1 mM DTT. Two bands are visible with $MW^{app}=33$ and 34.5 kD.

Lane 8: The $\alpha$-chain was incubated for 1 h at 37° C. with 1 mM DTT. Only one band is left migrating with $MW^{app}=34.5$ kD.

Lane 9: The $\alpha$-chain was incubated for 30 min at 95° C. in the presence of 10 mM DTT. The apparent molecular weight was identical to that in Lane 8.

Figures 1, 1B, 2, 3:
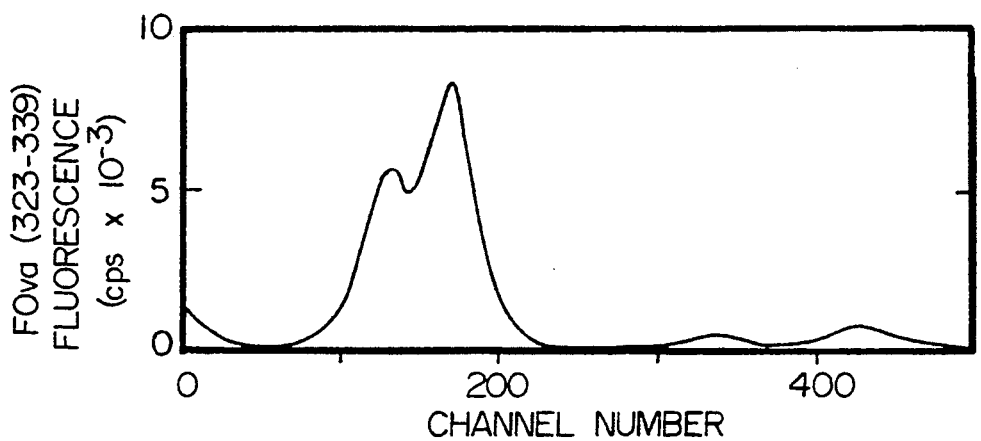

FIG. 3 demonstrates the effect of reoxidation to form a reassembled $IA^d$ $\alpha/\beta$ heterodimer from separate $\alpha$- and $\beta$-chains.

FIG. 3A shows a silver-stained SDS gel, wherein:

Lane 1: Molecular weight standards (see FIG. 2).

Lane 2: Electroeluted $\alpha$-chain.

Lane 3: Electroeluted $\beta$-chain.

Lane 4: $\alpha$- and $\beta$-chains were mixed and incubated for 1 h at 37° C.

Lane 5: $\alpha$- and $\beta$-chains were mixed and incubated for 1 h at 37° C. in the presence of 100 μM FOva(3-23-339).

Lanes 6 and 7: Identical to Lanes 4 and 5, but incubation was for 18 h.

Lane 8: $\alpha$- and $\beta$-chains were mixed and incubated for 1 h at 37° C. in the presence of 100 μM FOva(3-23-339) and 1 mM DTT.

Lane 9: $\alpha$- and $\beta$-chains were mixed and incubated for 1 h at 37° C. in the presence of 100 μM FOva(3-23-339) and 10 mM DTT.

Lane 10: $\alpha$- and $\beta$-chains were mixed, reduced for 1 h at 37° C. with 1 mM DTT, and reoxidized.

Lane 11: identical to Lane 10, but 10 mM DTT were used for reduction instead of 1 mM DTT.

Lanes 12 and 13: Identical to Lanes 10 and 11, but the samples were incubated for 1 h at 37° C. in 100 μM FOva(323-339) after reoxidation.

Figures 1, 3B:
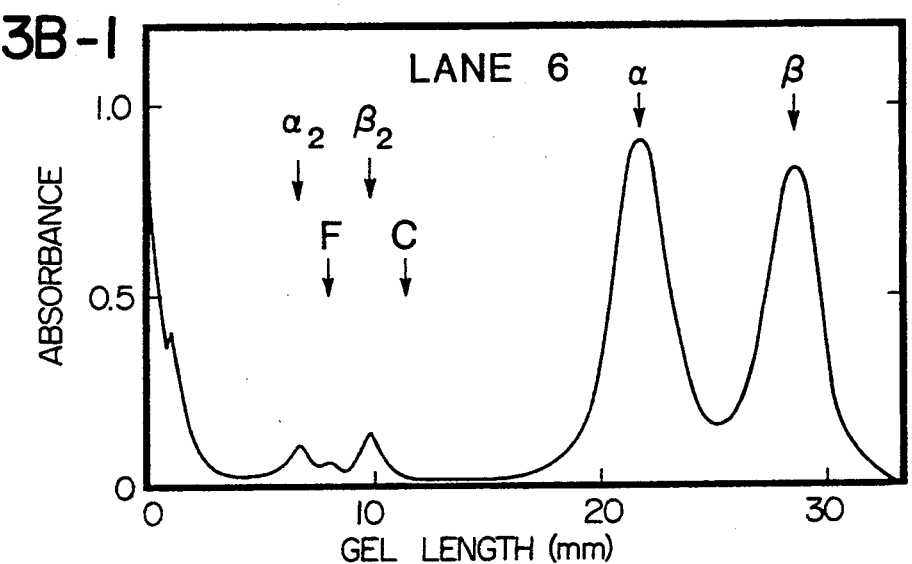
Figures 2, 3B:
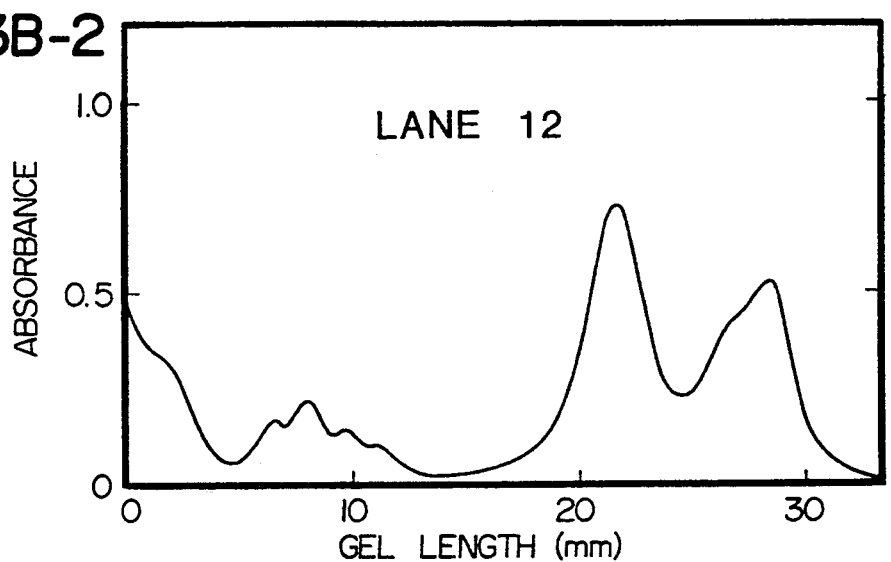
Figures 3, 3B:
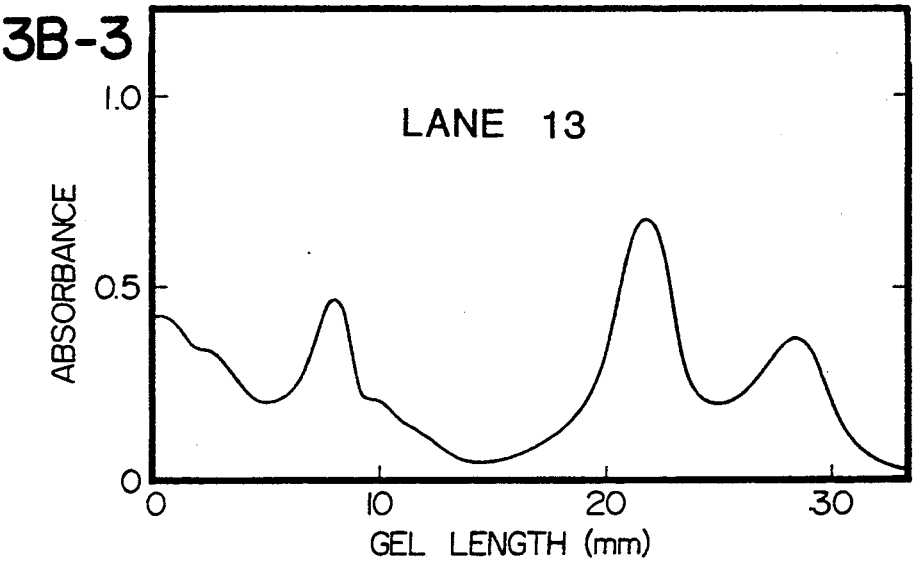

FIG. 3B shows scans from the gel shown in FIG. 3A. In order to quantify the relative protein concentrations, the gel shown in FIG. 3A was scanned on a gel scanner. The positions of the separate chains, the $\alpha/\beta$ heterodimeric compact (C) and floppy (F)conformations, and the homodimeric $\alpha$- and $\beta$-chains ($\alpha_2$ and $\beta_2$) are given. When the separate chains were isolated and incubated together without previous reduction and reoxidation, they did not reassemble to $\alpha/\beta$ heterodimers (Lane 6). Reassembly to the floppy (F) conformation was observed after reduction with 1 mM DTT or 10 mM DTT and reoxidation (Lanes 12 and 13, respectively).

A shoulder at the position corresponding to the compact (C) conformation is seen. A considerable amount of protein aggregated upon reoxidation to oligomers. The oligomers smear on the gel at apparent molecular weights higher than floppy (F) conformation. As the concentration of free $\beta$-chain was lower than the concentration of free $\alpha$-chain, it is assumed that most of the oligomers consist of $\beta$-chains.

Figures 1, 3C:
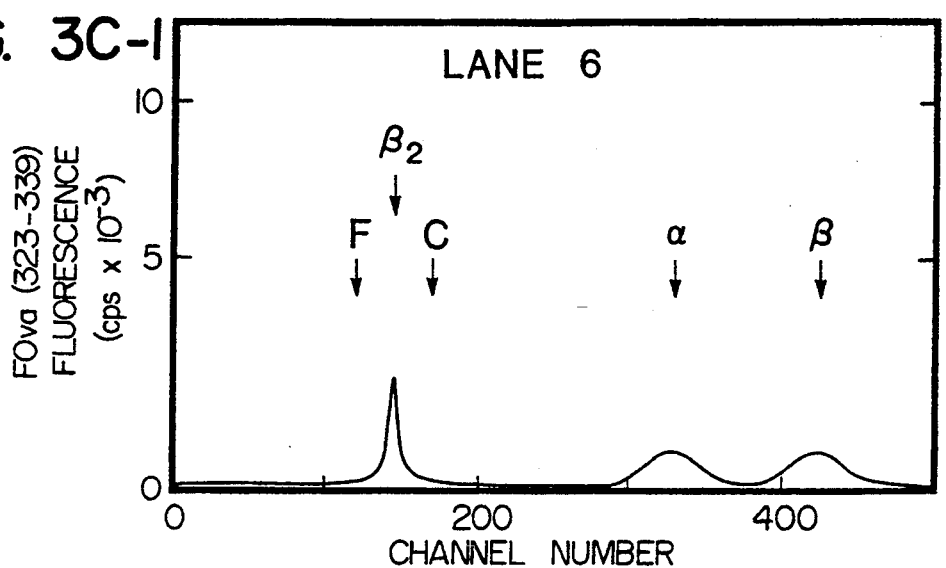
Figures 2, 3C:
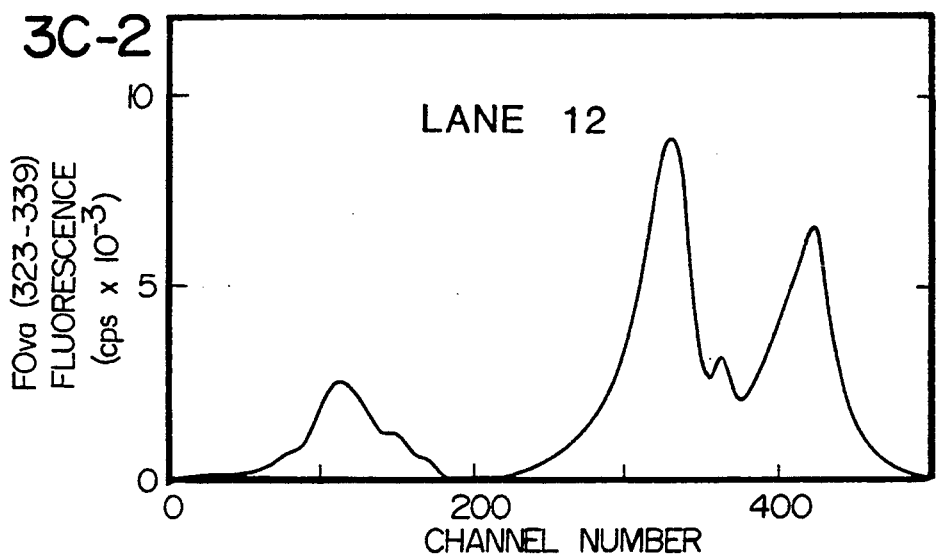
Figures 3, 3C:
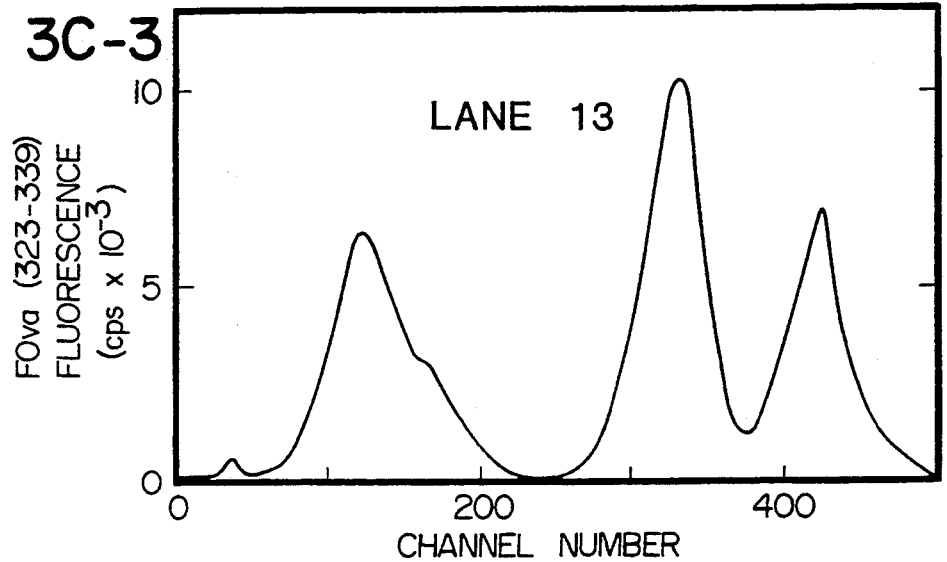

FIG. 3C shows scans for fluorescent peptides from the gel shown in FIG. 3A. The samples not subjected to reduction and reoxidation (Lane 6) bound small amounts of FOva(323-339). After reduction with 1 mM DTT or 10 mM DTT and reoxidation (Lanes 12 and 13, respectively), the peptide binding capacities of the separate $\alpha$- and $\beta$-chains was increased by factors of 9 and 11, respectively, as compared to Lane 6. The reassembled floppy (F) conformation was associated with high amounts of peptides. Although $\beta_2$ bound peptides (Lane 6), the $\beta$-chain oligomers did not (Lanes 12 and 13).

Figures 1, 1B, 2, 3, 4:
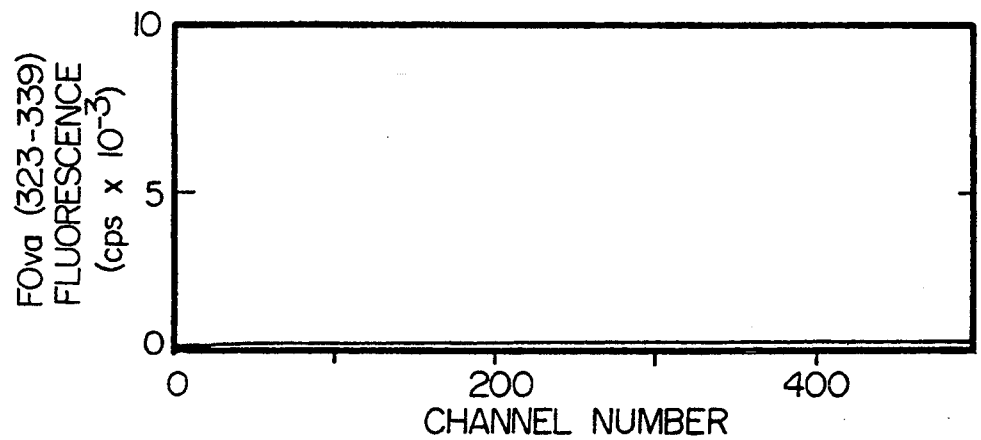
Figures 1, 1B, 2, 3, 4, 5:
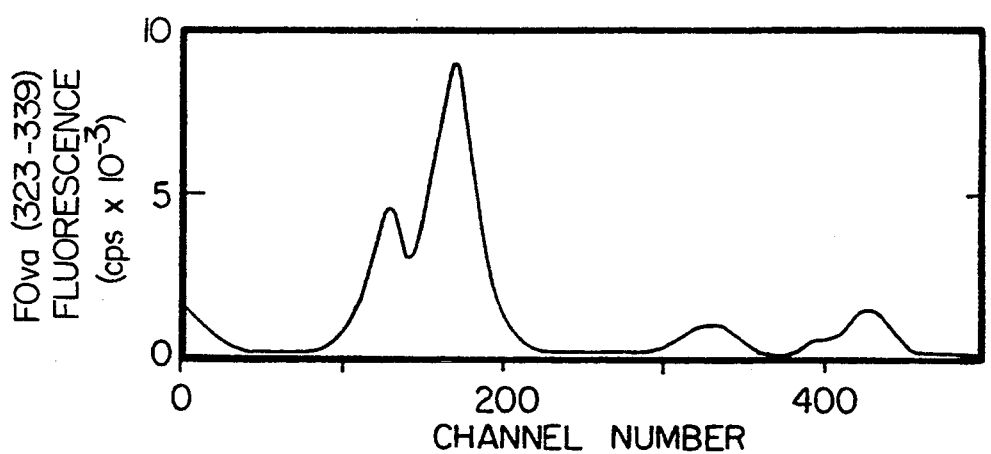

FIG. 4 demonstrates the reassembly of separate chains to the $\alpha/\beta$ heterodimeric floppy (F) and compact (C) conformations and shows a silver-stained SDS gel and western blots, wherein:

Lane 1: Silver-stained gel of a preparation of murine IA$^d$.

Lane 2: Western blot of the identical sample of Lane 1.

Lane 3: Western blot of refolded and reassembled separate chains.

The monoclonal antibody 28-16-8S, which recognizes an epitope expressed only by $\alpha/\beta$ heterodimers, was used for blotting. Although present in high concentrations, the separate chains are not recognized by 28-16-8S (compare Lanes 1 and 2). Lane 3 shows that the reassembly experiments yielded the floppy (F) and compact (C) conformations.

DETAILED DESCRIPTION OF THE INVENTION AND PREFERRED EMBODIMENTS

Structurally, MHC molecules are membrane-bound, heterodimeric glycoproteins. Class I MHC molecules consist of two polypeptide chains, a large $\alpha$-chain and a smaller $\beta_2$-microglobulin chain. The $\alpha$-chain is about 345 amino residues and has three extracellular globular regions, $\alpha_1$, $\alpha_2$, and $\alpha_3$, with a hydrophobic amino acid sequence near its carboxyl terminus by which it is anchored in the plasma membrane. There are two intrachain disulfide bonds formed from cysteine residues, one in the $\alpha_2$ region and one in the $\alpha_3$ region.

The class I molecule $\alpha$-chain and the $\beta_2$-microglobulin chain are noncovalently associated, and the latter is an extracellular, nonglycosylated protein 96 amino acids in length with one intrachain disulfide bond. It is thought that the antigen binding site is formed from the $\alpha_1$ and $\alpha_2$ domains of the class I MHC molecule, which are highly polymorphic.

Class II MHC molecules are similar to Class I MHC molecules in that they also are heterodimers with four extracellular domains. Class II MHC molecules have an $\alpha$-chain and a $\beta$-chain of approximately equal length, each having two domains designated $\alpha_1$, $\alpha_2$, $\beta_1$, and $\beta_2$. Disulfide bonds are present in the $\alpha_2$, $\beta_1$, and $\beta_2$ domains. The $\alpha_2$ and $\beta_2$ regions are anchored in the plasma membrane and appear to be highly conserved immunoglobulin-like domains. The aminoterminal domains of each chain, e and , are farthest from the cell membrane and are highly polymorphic. The interaction of these domains forms the antigen binding site of a class II MHC molecule.

For a general summary of the structure of MHC molecules as well as a discussion of their genetics, see Chapter 23 (The Generation of Immunological Specificity) in J. Watson, et al., *Molecular Biology of the Gene*, Benjamin/Cummings, Menlo Park (4th ed. 1987); Chapter 18 (The Immune System) in B. Alberts, *Molecular Biology of the Cell*, Garland, New York (2d ed. 1989); and Grey, H. M., et al., *Scientific American* November, 1989:56-64 (these publications are incorporated herein by reference).

Two distinct $\alpha/\beta$ heterodimeric conformations have been identified for class II MHC molecules, see Rothenhusler, B., et al., *Proc. Natl. Acad. Sci. USA* 7:352-354 (1990) (incorporated herein by reference).

The antigenic peptide forms a very stable complex with the MHC molecule, and this complex fits within a single recognition site in a T lymphocyte receptor. For discussion of T lymphocyte receptors, se, Rothbard, J. B., et al., *EMBO Journal* 7:93-100 (1988); Townsend, A., et al., *Ann. Rev. Immunol.* 7:601-624 (1989); Rothbard, J. B., et al., *Cell* 52:515-523 (1988); Lamb, J. R., et al., *EMBO Journal* 6:1245-1249 (1987); and Bodmer, H. C., Cell 52:253-258 (1988) (all of these publications are incorporated herein by reference).

As discussed above, in class I MHC molecules, the $\alpha 1$ and $\alpha 2$ regions may be responsible for binding whereas in class II MHC molecules the $\alpha_1$ and $\beta_1$ domains are involved. In both instances, the binding region appears to be a single site that is located in a groove wherein the sides are formed by $\alpha$-helices and the platform is formed by $\beta$-strands. For a hypothetical model of the antigen binding site of class II MHC molecules, see Brown, J. H., et al., *Nature* 332:845-50 (1988)(incorporated herein by reference). See also Chen, B. P., *Nature* 337:743-745 (1989) for a discussion of the direct binding of influenza peptides to class I MHC molecules.

Peptide binding occurs in both the compact (C) and floppy (F) conformations of the class II MHC $\alpha/\beta$ heterodimer; separate and isolated $\alpha$-and $\beta$-chains can specifically bind antigenic peptides as well, see Rothenhäusler, B., et al., *Proc. Natl. Acad. Sci. USA* 87:352-54 (1990) (incorporated herein by reference). In addition to binding antigenic peptides, class II MHC molecules bind with autologous, or "self" peptides, see Buus, S., et al., *Science* 242:1045-1047 (1988); Demotz, et al., *Nature* 342:682-684 (1989) (these publications are incorporated herein by reference).

The stability of the antigenic peptide and the MHC molecule is reflected in the extremely slow off-rate of the peptide. This feature promotes functioning of MHC molecules in the cell. It is known that antigenic peptides are bound to an MHC molecule in an intracellular compartment, then the MHC molecule-antigenic peptide complex is transported to the cell surface, where it "waits" for a specific T lymphocyte. If the antigenic peptide was not trapped or bound with a slow off-rate, it would disassociate during export or when it was in the plasma membrane.

It is hypothesized herein, but should not be limiting to the present invention, that folding, assembly and peptide binding may take place in the same cellular compartment. This theory is consistent with the finding discussed above that peptides may bind specifically to separate $\alpha$- or $\beta$-chains, see Rothenhusler, B., et al., *Proc. Natl. Acad. Sci. USA* 83:352-354 (1990) (incorporated herein by reference). The biological task of MHC molecules is to bind a variety of antigenic peptides and to retain each of them for extended periods of time. When the mechanism of peptide-MHC assembly is ultimately understood, the term "trapping site" may be more appropriate than "binding site."

The present invention includes processes for increasing antigen binding capacity of a class I or class II MHC molecule or chain thereof. These processes comprise the steps of treating an antigen-bound MHC molecule or chain with an effective amount of an unfolding agent, preferably a reducing agent such as dithiothreitol that cleaves disulfide bonds in the MHC molecule, to release the undesired antigen from the MHC molecule or chain; removing the unfolding agent and the released antigen;

and treating the antigen-free MHC molecule or chain with an effective amount of a refolding agent, preferably an oxidizing agent to reform the disulfide bonds, under suitable conditions whereby a functional MHC molecule or chain is produced. In one embodiment, desired specific antigens can then be added to the MHC molecules. Both the $\alpha/\beta$ heterodimer and the separate $\alpha$- and $\beta$-chains resulting from the present processes bind significantly higher amounts of antigen after having been unfolded and refolded, as compared to an untreated MHC molecule or chain thereof.

MHC molecules can be either from class I or class II or mixtures thereof. Additionally, separate class I $\alpha$-chains or class II $\alpha$- or $\beta$-chains or mixtures thereof can be used alone or in combination with whole MHC molecules. Truncated MHC molecules wherein the membrane-bound carboxyl terminals of the chains have been removed can also be used. The MHC molecules can be either of the compact (C) conformation or of the floppy (F) conformation or a mixture thereof. Given the variety of specificities found in MHC molecules and their chains, the type of MHC molecule(s) or chain(s) thereof that are selected will depend upon the research project or therapeutic or diagnostic regime employed.

Sources of MHC molecules are familiar to those skilled in the art and include affinity chromatography using cell lines or recombinant DNA techniques. As an example, but not limiting to the present invention, murine IAd, which is a class II MHC molecule, can be affinity purified from cells using an antibody that recognizes epitopes expressed only by $\alpha/\beta$ heterodimers. For a discussion of MHC purification, see, e.g., Watts, T. H., et al., *Ann. Rev. Immunol.* 5:461–475 (1987); Watts, T. H., et al., *Proc. Natl. Acad. Sci. USA* 81:7564–7568 (1984); Watts, T. H., et al., *Proc. Natl. Acad. Sci. USA* 82:5480–5484 (1985) (all of these publications are incorporated herein by reference). See also Saito, et al., U.S. Pat. No. 4,874,845 (incorporated herein by reference), for a discussion of the recombinant techniques and T lymphocyte receptors).

Antigen, as used herein, refers to any substance that can fit into the binding site of a class I or class II MHC molecule or a chain thereof. Usually, this will be a peptide fragment but, depending upon the antigen encountered, it can include whatever an antigen presenting cell (APC) puts on its surface, for example, a polysaccharide fragment may be presented. Antigens can be either foreign or "self" (autologous).

In the processes of the present invention, an antigen-bound MHC molecule or a chain thereof is treated with an effective amount of an unfolding agent. An effective amount of a unfolding agent is that amount necessary for the MHC molecule or chain to release substantially all of the bound antigen. The effective amount will vary depending upon the selected unfolding agent, the concentration of MHC molecules, the reaction conditions, etc. In general, an amount that releases greater than 70% of bound antigens is preferred, with an amount that releases greater than 90% of bound antigens being more preferred, and an amount that releases greater than 99% being most preferred.

The unfolding (chaotropical) agent includes any chemical or condition, or combination thereof, that induces release of an antigen from a class I and/or class II MHC molecule and/or chain thereof. Such release can occur through modification of the structure and flexibility of the MHC molecule or chain. Reduction of the intrachain disulfide bonds can release the antigen, in which case the unfolding agent is referred to as a reducing agent. Additionally, a relaxing of the secondary structure of the molecule or chain can release the antigen. In the latter situation, the disulfide bonds may remain intact, but the integrity of the molecule or chain is disturbed so that antigen binding is prohibited or significantly decreased.

Preferred unfolding agents that reduce disulfide bonds are dithiothreitol (DTT), dithioerythritol, and mercaptoethanol; with DTT most preferred. Other reducing agents $NaBH_4$, $LiAlH_4$, $H_2$ (used catalytically), P (red), Zn (in dilute acid), hydroquinone, and $(C_6H_5)_3P$ (in water). Many other reducing agents will be apparent to one skilled in the art and can be used singularly or in combination.

Reaction conditions will vary widely depending upon the unfolding agent selected and its effective amount. These conditions include temperature; pH; agitation, if necessary; time period; etc. Those skilled in the art will recognize that by adjusting one reaction parameter, other parameters may need to be modified. For DTT, a concentration range from about 1 mM to about 10 mM is preferred with a treatment time period of approximately 1 hour at a temperature of about 37° C. being most preferred. Obviously, lower concentration ranges of DTT, as well as for other unfolding agents, may require longer treatment periods, such as from approximately 6 to 8 hours or even longer, and temperature ranges may also vary. Using the procedures described in the Experimental section below, it can be determined whether the unfolding agent has released substantially all of the bound antigen.

It is not necessary to completely unfold and refold the MHC molecule in order to increase its antigen binding capacity. As shown in the Examples below, the floppy conformation (F) of a murine $IA^d$ class II MHC molecule disassembled upon reduction with DTT and was restored from the separate chains upon reoxidation; the compact conformation (C) remained unchanged under the same conditions. However, the compact (C) conformation lost all of its antigenic peptides upon reduction, and bound 2.5 fold the amount of FOva(323–339), which is a small peptide (17 amino acids) of chicken ovalbumin that binds MHC molecules, after reoxidation (see Table I below). The disulfide bonds of compact (C) conformation may be reduced by DTT, but yet the protein may not unfold.

It is known that the formation of disulfide bonds contributes considerably to the free energy stabilizing secondary structures, see Matsumura, M., et al., Nature 342:291–29 (1989) (incorporated herein by reference), but, on the other hand, much of free energy is determined by noncovalent interactions. Because one $\alpha/\beta$ heterodimeric conformation may unfold upon reduction whereas the other conformation may be stable, MHC molecules can serve as a model for studying the stability of proteins. The fact that compact (C) MHC molecules may release antigens without disassembly can be hypothesized, but not limiting to the present invention, as resulting from an increased flexibility, despite an unaltered mean structure, due to reduced disulfide bonds that may allow the antigen to disassociate with a fast off-rate. If the MHC molecule is rigid, i.e., with oxidized disulfide bonds, the antigen disassociates at an extraordinarily slow rate.

Unfolding agents of the present invention also include agents that do not reduce disulfide bonds but unfold the remainder of the MHC molecule or chain thereof. Such agents include urea, guanidinium chloride, thiocyanate, detergents (such as SDS, dodecyl-$\beta$-D-maltoside (DM), TritonX100, Nonidet P40), low pH (<3) (see Demotz, S., et al., *Nature* 342:682–684 (1989) (incorporated herein by reference)), high pH (>12), and elevated temperatures. Detergents serve to stabilize membrane-bound proteins such as MHC molecules. Elevated temperatures are particularly effective when combined with the above detergents and agents that induce low pH. Such agents can be used singularly or in combination. Simultaneous use of such unfolding agents that do not reduce disulfide bonds with reducing agents is also an effective means to unfold MHC molecules and chains thereof. An example of such a combination is the use of SDS or urea with DTT. Additionally, physical agents, such as a change in pH can also be combined.

Once the antigen-bound MHC molecule or chain thereof has been treated with an unfolding agent, the unfolding agent and the released antigen are removed. This can be accomplished by a variety of means, including dialysis, gel filtration, ion exchange or affinity chromatography, electrophoresis, ultrafiltration, ultracentrifugation, chemical, or enzymatic reactions (including neutralization), or combinations thereof.

Next, the unbound MHC molecule or chain thereof is treated with an effective amount of a refolding agent whereby a functional MHC molecule or chain is produced. The term "functional MHC molecule or chain" refers to the ability to bind a peptide. An effective amount of a refolding agent is that amount necessary for the MHC molecule or chain to regain the capacity to bind an antigen.

Therefore, the effective amount will vary depending upon the concentrations of antigens and MHC molecules or chains, the reaction conditions, the refolding agent, etc. Reaction conditions will vary widely and one of ordinary skill in the art will be aware of them. In part, the binding of an antigen with an MHC molecule or chain is due to the kinetics and thermodynamics of antigen-MHC molecule reaction, and ways to increase the chances of antigens and MHC molecules colliding are known in the pertinent field.

A refolding agent can be any chemical or condition, or combination thereof, that produces a functional MHC molecule or chain. Such refolding produces MHC chains with native structure and can occur by forming intrachain disulfide bonds through oxidation or, if such bonds have not been disturbed, by causing the secondary structure of the MHC molecule to reform. Examples of refolding agents include $O_2$, $K_3Fe(CN)_6$, $HgCl_2$, $H_2O_2$, quinones, $Br_2$, $TlAc_3$, MeSOF$_2$, NO, and $NO_2$. Preferred compositions are $O_2$, $K_3Fe(CN)_6$, and $HgCl_2$, with the most preferred being $O_2$ introduced by dialysis in an air-saturated buffer for approximately 12–18 hours. For a guide to the folding and association of proteins in general, see Jaenicke, R., *Prog. Biophys. molec. Biol.* 49:117–237 (1987) (incorporated herein by reference).

As with refolding, the flexibility of MHC chains also plays a major role in the reassembly of separate $\alpha$- and $\beta$-chains to an class II $\alpha/\beta$ heterodimer. Such reassembly occurs simultaneously with refolding. As shown in the following Examples, chains did not reassemble when they were in the folded state. It is known that several proteins do not reassemble to homo- or heterodimeric conformations when the subunits are folded, but may be reassembled when they are refolded simultaneously, see Huber, R., *Angew. Chem. Internatl. Edit.* 27:79–88 (1988) (incorporated herein by reference). Similar to the reassembly of heavy and light chains of immunoglobulin Fab fragments, refolding and concomitant reassembly resulted in the following Examples when unfolded chains were used, see Björk, I., et al., *Biochemistry*, 10:1289–1295 (1971) (incorporated herein by reference). High flexibility of the chains may be a factor in successful reassembly.

Figuratively, the two chains may refold and synchronously reassemble like a zipper. Once the heterodimer is formed, it is very stable because the chains are hooked into each other. This picture, although not limiting to the present invention, is consistent with the high stability of MHC molecules observed experimentally by the present inventors. Such rigid chains hooked into each other may act as a trap for bound antigens, which may explain the slow off-rates seen in MHC molecules. FIG. 2 demonstrates the unfolding of separate $\alpha$- and $\beta$-chains by use of a western blot.

The present invention also comprises processes for adding a desired specific antigen to a functional MHC molecule or chain thereof, produced as described above. These processes have utility in therapeutic administrations and diagnostics wherein a specific treatment or assay is envisioned. The desired specific antigen is added to the MHC molecules or chains thereof that are substantially free of undesired antigens. By specific, it is meant an antigen that can bind with an MHC molecule or chain thereof and that the MHC-antigen complex can then bind with a T lymphocyte receptor. An example of a desired specific antigen includes, but is not limited to, peptide fragments.

Also included in this invention are processes for separating an antigen from a MHC molecule or chain thereof other than by lowering pH, comprising treating the molecule or chain with an effective amount of an unfolding agent. The unfolding agents and their effective amounts are defined above. An unfolding agent that is a reducing agent is preferred, with DTT being most preferred. In these processes, the MHC molecule or chain thereof is not refolded. Such processes have utility in, for example, the storage of antigen-free MHC molecules or chains thereof for later usage. Additionally, the released antigen may be recovered for further identification and analysis.

The present invention also comprises compositions produced by the processes discussed above.

Compositions comprising MHC molecules or chains thereof that are substantially free of antigens are also included in this invention. Usually, substantially free refers to greater than 70%, with greater than 90% more preferred, and greater than 99% most preferred. These compositions are in a substantially pure form as they are substantially free of antigens. Such purity can be important for therapeutical and analytical purposes.

The MHC molecule or chain thereof can be a class I or class II molecule or any of the chain components or a mixture thereof. Additionally, the MHC molecule can be in a floppy (F) or compact (C) conformation.

A composition comprising an MHC molecule or chain thereof that is substantially free of antigens is a preferred reagent for screening purposes, such as screening for new therapeutic agents. Thus, an MHC molecule or chain thereof whose binding site is substantially free of antigenic peptides can be used to screen for peptides or other substances that bind with the MHC molecule or chain thereof. Furthermore, an MHC molecule or chain to which a specific desired antigen is bound can be used to screen for potential therapeutic agents that displace the specific antigens. In all such screening procedures, pure MHC molecules or chains are preferred, both from the point of specificity as well as sensitivity.

By introducing a labelled (tagged), e.g., radioactive or fluorescent, peptide fragment to MHC molecules or chains thereof that are substantially free of antigens, specific T lymphocyte clones can be assayed. The T lymphocyte receptor and MHC-peptide complex will bind if specificity exists, and the resultant labelled cell can be detected by methods known in the art.

A composition comprising an MHC molecule or chain thereof that is substantially free of undesired antigens to which a desired specific antigen, such as a peptide, is bound, can be used as a therapeutic composition when combined with a pharmaceutically acceptable carrier. Such carriers are known in the art and may be any compatible, nontoxic substance suitable for the delivery of MHC molecules to the patient. Sterile water, alcohol, fats, waxes, and inert solids may be included, as well as adjuvants, if desired. The concentration of MHC molecule in these formulations can vary widely, depending upon the condition to be treated, and the patient's medical history.

Such compositions can be employed to treat a patient with an autoimmune condition, wherein the MHC-antigen complex binds to T lymphocyte receptors and inhibits or tolerates. For a specific example of such a disease, see, e.g., Kumar, V., et al., *Proc. Natl. Acad. Sci. USA* 87:1337–1341 (1990) (incorporated herein by reference).

A therapeutically effective amount of a present composition is administered to the patient, preferably parenterally, that is, subcutaneously, intramuscularly, or intravenously. Actual methods for preparing administrable compositions, depending upon the made of administration, are readily available to those skilled in the art and are described in more detail in, for example, *Remington's Pharmaceutical Science,* Mack Publishing, Easton, Pa. (15 ed. 1980) (incorporated herein by reference).

Additionally, compositions of the present invention can be conjugated with a cytotoxic agent and a pharmaceutically acceptable carrier, the latter of which is discussed above. Cytotoxic agents are known in the art and include, but are not limited to, various radioisotopes, the alkaloid vindesine, the ricin A-chain, daunomycin, and the like. Such agents can also include antimicrobial substances, including antiviral compositions, directed at a specific antigenic source.

Antibodies can be prepared by injecting MHC molecules or chains thereof into a foreign host, in accordance with conventional techniques. Alternatively, monoclonal antibodies may be prepared, following the technique elaborated in Kohler & Milstein, *Nature* 256:495 (1975). Of particular interest to the present invention is the monoclonal antibody, 28-18-85, see Ozato, K., et al., *J. Immunol.* 126:317–321 (1979) (incorporated herein by reference), which recognizes an epitope expressed only by $\alpha/\beta$ heterodimers, as shown in FIG. 4.

Once the antibodies are having suitable specificity have been produced, a wide variety of immunological assay methods may be utilized to ascertain the presence of such MHC molecules or chains thereof. Numerous competitive and non-competitive protein binding assays have been described in the literature, and a large number are commercially available. Typically, the assays entail the use of labels on antibodies and these include radionuclides, fluorescors, enzymes, enzyme substrates, enzyme cofactors, enzyme inhibitors, etc. In the Examples below, western blotting using an alkaline phosphatase conjugated goat anti-mouse antibody was used for detection.

Thus, a variety of therapeutic and screening utilities can be envisioned by one skilled in the art using the compositions of MHC molecules and/or chains thereof of the present invention, alone or in combination with other compositions and agents.

It is to be understood that the above description and the following experimental section are intended to be illustrative and not restrictive. Many variations and applications will be readily apparent to one of ordinary skill in the art upon reviewing this disclosure. Although slight modifications of experimental details may have to be introduced for haplotypes other than murine $IA^d$ class II MHC molecules, the present processes provide a means to overcome the well-known problems of antigens, including autologous peptides, occupying the binding site.

In the following Examples, it is demonstrated that (1) reduction of disulfide bonds of murine $IA^d$ class II MHC molecules releases previously bound peptides; (2) separate chains may be unfolded and then refolded and reassembled to the floppy (F) conformation; and (3) refolding and reoxidation of disulfide bonds of both the $\alpha/\beta$ heterodimers and the separate $\alpha$- and $\beta$-chains lead to an increased antigen binding capacity.

EXAMPLES

Sample Preparation

Murine $IA^d$ which is a class II MHC molecule was affinity purified from A20.1.11 cells (available from American Type Culture Collection as deposit no. TIB 208) using the antibody MK-D6 (available from American Type Culture Collection as deposit no. HB 3), see Braunstein, N. S., et al., *Proc. Natl. Acad. Sci. USA* 84:2921–2925 (1987) (incorporated herein by reference), as described in Rothenhäusler, B., et al., *Proc. Natl. Acad. Sci. USA* 87:352–354 (1990) (incorporated herein by reference). 30 mM octyl-$\beta$-D-glucopyranoside was replaced by 2 mM dodecyl-$\beta$-D maltoside (DM) (Calbiochem, La Jolla, Calif.), which has a lower critical micellar concentration. The $IA^d$-containing fractions were pooled and dialyzed in 10 mM Tris/HCl, pH 8.3, 150 mM NaCl, 0.02% $NAN_3$, 2 mM DM over night.

This preparation, which is referred to as $IA^d$, contained the compact (C) and floppy conformations (F) and separate $\alpha$- and $\beta$-chains of class II MHC molecules. To isolate the $\alpha$- and $\beta$-chains separately, purified $IA^d$ was run on preparative SDS gels, omitting $\beta$-mercaptoethanol, and not boiling the samples. The $\alpha$- and $\beta$-chains were electroeluted, see Hunkapiller, M. W., *Meth. Enzymol.* 91:227–236 (1983) (incorporated herein by reference), from these gels in 25 mM Tris, 0.2M glycine, pH 8.2, 0.1% SDS.

Reduction and Reoxidation Reactions $IA^d$ (30 $\mu$g/ml) was reduced with 1 mM and 10 mM DTT in 10 mM Tris/HCl pH 8.3, 150 mM NaCl, 0.02% $NAN_3$, 2 mM DM by incubation for 1 h at 37° C. The $\alpha$- and $\beta$-chains (20 $\mu$g/ml each) were incubated for 1 h at 37° C. in 1 mM or 10 mM DTT in 25 mM Tris, 0.2M glycine, pH 8.2, 0.1% SDS either separately or after mixing equal amounts. For reoxidation, the reduced samples were dialyzed in the at least 1000 fold volume of 10 mM Tris/HCl pH 8.3, 150 mM NaCl, 0.02% NAN₃, 2 mM DM for 18 h. 9DC DiaCell ™ Dialysis Capsules equipped with Spectrapor dialysis tubings with a molecular weight. cutoff of 12 kD were used. The sample volume was typically 50 µl. A basin with a large enough surface to allow for oxygen saturation of the buffer was used.

Peptide Incubation and Analytical Gel Electrophores $IA^d$ or the α- and β-chains were incubated with 100 µM FOva(323-339) for 1 h at 37° C. before reduction or after reoxidation. Reduction was performed after incubation with 100 µM FOva(323-339). After the incubations, the samples were loaded immediately on 12.5% SDS gels. Prior to fixation and silver staining, the gels were scanned for fluorescent peptides on a fluorescence microscope as described in Rothenhäusler, B., et al., Proc. Natl. Acad. Sci. USA 83:352-354 (1990) (incorporated herein by reference). The gels were silver-stained, see Heukeshoven, J., et al., Electrophoresis 6:103-112 (1985) (incorporated herein by reference), and relative protein concentrations determined by scanning the silver-stained gels on a LKB UltroScan XL Laser Scanner. The scans for fluorescent peptides and for silver-stained proteins were corrected for background.

Western Blotting

Proteins were transferred from SDS gels to nitrocellulose membranes overnight at 30 V in 20 mM Tris, 150 mM glycine, pH 8.0. MHC heterodimers were detected with the monoclonal antibody 28-16-8S (available from American Type Culture Collection as deposit no. HB 35), see Ozato, K., et al., J. Immunol. 126:317-321 (1979) (incorporated herein by reference). An alkaline phosphatase conjugated goat anti-mouse antibody (Sigma, St. Louis, Mo.) was used for detection, and 0.1 mg/ml nitro blue tetrazolium and 0.05 mg/ml 5-bromo-4-chloro-indolylphosphate in 50 mM sodium carbonate buffer, pH 9.5, 2 mM MgSO₄ was used for staining.

Results

FIG. 1 shows the effect of reduction with 1 mM and 10 mM DTT and reoxidation on $IA^d$. FIG. 1A shows the silver-stained SDS gels and FIG. 1B shows the corresponding scans for fluorescent peptides. The relative distribution of the two α/β heterodimeric conformations, compact (C) and floppy (F), and the separate α- and β-chains as revealed by scanning the silver-stained gel on a gel scanner, and the relative amount of peptide bound to each of these conformations are given in Table I below.

TABLE I

| | F | C | α | β |
|---|---|---|---|---|
| Relative Protein Concentrations (absorbance × mm) | | | | |
| No treatment | 1.23 | 2.19 | 0.15 | 0.13 |
| Reduction 1 mM DTT | 0.25 | 1.86 | 0.41 | 0.62 |
| Reoxidation | 1.07 | 1.40 | 0.10 | 0.13 |
| Reduction 10 mM DTT | 0.43 | 1.87 | 0.76 | 1.05 |
| Reoxidation | 1.26 | 2.18 | 0.25 | 0.28 |
| Relative Fluorescence Intensities (cps × 10⁻³ × channels) | | | | |
| No treatment | 4.9 | 12.2 | <1.5 | <2.0 |
| Reduction 1 Mm DTT | <0.5 | 0.9 | <1.5 | <2.0 |
| Reoxidation | 19.8 | 29.0 | 2.0 | 3.0 |
| Reduction 10 mM DTT | <0.5 | <0.5 | <1.5 | <2.0 |
| Reoxidation | 16.0 | 32.0 | 4.6 | 6.6 |

In Table I, the relative protein concentrations and fluorescence intensities of the samples of FIGS. 1A and B are given. The relative protein concentrations were determined by scanning the silver-stained gel on a gel scanner. The numbers were obtained by integrating the area under the peaks. Relative fluorescence intensities were determined by scanning the gel on a fluorescence microscope prior to fixation. The numbers were obtained by multiplying the peak maximum with the half width of peak. FOva(323-339) was smeared over the gel. The fluorescence background increased with the length of the gel. Therefore, the detection limit for the β-chain is higher than for the α-chain, which again is higher than for floppy (F) conformation.

$IA^d$ was incubated with 100 µM FOva(323-339) for 1 h at 37° C. (FIGS. 1A and B, Lane 1). Scanning of the silver-stained gel on a gel scanner revealed a relative distribution of floppy:compact: α chain:β chain = 1.23:2.19:0.15:0.13 (Table I). As shown in FIG. 1B, Lane 1, and reported in Rothenhusler, B., et al., Proc. Natl. Acad. Sci. USA 83:352-354 (1990) (incorporated herein by reference), all of these conformations bind specific peptides.

However, the relative concentrations of separate chains in the present preparation was particularly low. Reduction of the disulfide bonds with 1 mM and 10 mM DTT led, in both experiments, to the complete loss of peptides bound to $IA^d$ (FIG. 1B, Lanes 2 and 4, respectively and Table I). Only a small amount of peptide remained bound to the compact conformation after reduction with 1 mM DTT, which completely disappeared upon reduction with 10 mM DTT. This indicates that compact (C) is the most stable conformation. The effect of reduction on the secondary structure can be seen in the silver-stained gel: whereas the compact (C) conformation is unaltered, floppy (F) conformation disappeared almost completely (FIG. 1A, Lanes 2 and 4). Most of floppy (F) conformation disassembled to separate chains (Table I). Both the separate α- and β-chain migrated at positions corresponding to higher apparent molecular weights, indicating unfolding of the proteins.

Reoxidation by dialysis in air saturated buffer restored not only the floppy (F) conformation from the separate chains (Table I) and the folded conformation of both the α- and the β-chain (FIG. 1A, Lanes 3 and 5). In addition, peptide binding was restored (FIG. 1B, Lanes 3 and 5 and Table I).

Importantly, the amount of peptide bound to each of these conformations was significantly higher (Table I). The fluorescence associated with floppy (F) conformation rose from 4,900 cps × channels of the untreated sample to 19,800 cps × channels and 16,000 cps × channels of the reduced and reoxidized samples, respectively. Although less pronounced, a significant increase of peptide binding to the compact (C) conformation and to the separate α- and β-chains was observed. These results are interpreted, but do not limit the present invention, as being related to the release of previously bound peptides by reduction and removal by dialysis. Reoxidation and refolding yields MHC molecules lacking bound peptides. Therefore more binding sites are accessible for FOva(323-339). With the particular preparation used herein, it was found that the peptide binding of all conformations was increased by a factor of greater than 2.5 after reduction with 10 mM DTT and reoxidation (see Table I). However, other preparations showed peptide binding capacities to be increased by a factor of ten or more.

In order to investigate the conformational changes and enhanced peptide binding capacity of $IA^d$ after reduction and reoxidation in more detail, the separate $\alpha$- and $\beta$-chains were isolated by electroelution from preparative SDS gels. As shown in FIG. 2, the $\beta$-chain migrated with $MW^{app}=27.5$ kD (Lane 1). After reduction with 1 mM DTT (Lane 2), 35% of this chain migrated at $MW^{app}=28.5$ kD and 25% with $MW^{app}=30$ kD. After reduction with 10 mM DTT, 100% of the $\beta$-chain migrated at $MW^{app}=27.5$ kD (Lane 3). Again, boiling did not alter the apparent molecular weight (Lane 4).

As also shown in FIG. 2, the $\alpha$-chain migrated with $MW^{app}=33$ kD (Lane 6). After reduction with 1 mM DTT for 1 h at 37° C., 75% of this chain migrated at $MW^{app}=34.5$ kD (Lane 7). After reduction with 10 mM DTT, 100% of the $\alpha$-chain migrated at $MW^{app}=34.5$ kD (Lane 8). Boiling for 30 min in 2% SDS in the presence of 10 mM DTT did not alter the apparent molecular weight (Lane 9).

Thus, both chain migrated with higher apparent molecular weights after reduction. This is interpreted, but not limiting to the present invention, as due to an increased effective volume of the proteins, i.e., to a partial or complete unfolding of their secondary structure. As the unfolding of the $\beta$-chain occurs in a two-step reaction, it is assumed that one of the disulfide bonds of the $\beta$-chain has a higher redox potential than that of the other bond.

Boiling in SDS in the presence of high concentrations of DTT leads to a complete unfolding of the secondary structure. Therefore, it is postulated that, upon incubation in 10 mM DTT for 1 h at 37° C., $IA^d$ not only disassembles into separate chains but those chains also unfold, possibly even to a random conformation. This interpretation, although not limiting to the present invention, easily explains the fact that reduced $IA^d$ does not bind peptides (FIG. 1).

In this experiment, the compact (C) conformation was found to be somewhat resistant to reduction. This might be explained, but does not limit the present invention, by assuming a higher redox potential of one or more of the disulfide bonds in this $\alpha/\beta$ heterodimeric conformation than in the floppy (F) conformation or in the separate chains. Alternatively, the disulfide bonds might be reduced, but the noncovalent interaction between the chains is stronger than in the floppy (F) conformation, thus preventing disassembly and unfolding. Another possibility is that the disulfide bonds might be reduced, but the noncovalent interaction between the chains is stronger than in the floppy (F) conformation, thus preventing disassembly and unfolding. Boiling in SDS in the presence of DTT or mercaptoethanol does cause the compact (C) conformation to disassemble and unfold.

The separate chains can be reassembled to the $\alpha/\beta$ heterodimer. FIG. 3A shows the electroeluted $\alpha$- and $\beta$-chains in Lanes 2 and 3. A small fraction of both the $\alpha$- and $\beta$-chains dimerized, migrating with $MW^{app}=68$ kD and 56.5 kD, respectively. This is analogous to the dimerization of immunoglobulin heavy and light chains, see Björk, I., et al., *Biochemistry* 10:1289–1295 (1971). The chains were mixed and incubated at 37° C. with and without peptide for 1 h and 18 h (Lanes 4–7). Under these conditions, reassembly was not achieved. The mixed, separate chains were reduced with 1 and 10 mM DTT for 1 h at 37° C. (Lane 8 and 9, respectively), thus unfolding the proteins.

Reoxidation by dialysis in air saturated buffer (Lanes 10–13) not only refolded the separate chains as evidenced from their lower apparent molecular weights, but also yielded considerable amounts of $\alpha/\beta$ heterodimers migrating with $MW^{app}$ 64 kD. This corresponded to the floppy (F) conformation and was distinctly different from the $\alpha$- and $\beta$-chain dimers discussed above. The yields of reassembled $\alpha/\beta$ heterodimer were 8% after reduction with 1 mM DTT and reoxidation (Lane 10), 18% after reduction with 10 mM DTT and reoxidation (Lane 11), 5% after reduction with 1 mM DTT and incubation with 100 $\mu$M FOva(3-23–339) following the reoxidation (Lane 12), and 17% after reduction with 10 mM DTT and incubation with 100 $\mu$M FOva(323–339) following the reoxidation (Lane 13). Thus, the yield was significantly higher when the proteins were first unfolded completely, indicating that reassembly occurs simultaneously with refolding. The incubation with peptides had no pronounced influence on the reassembly efficiency.

FIGS. 3B and 3C show scans for proteins and for fluorescent peptides of Lanes 6, 12, and 13 of FIG. 3A. The positions of separate chains, homodimers, and the compact (C) and floppy (F) heterodimers are indicated. FIG. 3B provides clear evidence that reassembly only occurs if the separate chains have been previously unfolded. In Lane 6, folded separate chains were incubated. In Lanes 12 and 13, the chains were first unfolded and reassembled during refolding to yield predominantly floppy (f) and, to some extent, compact (C) conformations. It has been shown that MHC molecules disassemble in a consecutive reaction: compact→floppy→disassembled chains. The results presented herein indicate, but do not limit the present invention, that the separate chains first reassemble to yield floppy (F) conformation, then the reaction proceeds to yield compact (C) conformation. Therefore, it is the reverse reaction of the disassembly reaction.

At molecular weights higher than those of floppy (F) conformation, aggregated chains can be seen. However, comparison with FIG. 3C shows that those aggregates do not bind peptides, and thus may be aggregated in an unfolded state. As the concentration of free $\beta$-chain is decreased compared to the $\alpha$-chain, it is assumed that the high moleculear weight aggregates are $\beta$-chain oligomers.

The samples of Lanes 6, 12, and 13 were incubated with FOva(323–339) under identical conditions directly before applying them to the gel. After normalizing the protein concentrations using the scans for proteins shown in FIG. 3B, which was necessary because the overall recovery was not quantitative and the $\beta$-chains oligomerized, the peptide binding capactiy of the $\alpha$- and $\beta$-chains increased by factors of 11 and 9, respectively, in the particular preparation used herein.

To obtain additional evidence that the product of the reassembly experiment is the heterodimeric floppy conformation (F), the monoclonal antibody 28-16-8S, see Ozato, K., et al., *J. Immunol.* 126:317–321 (1979) (incorporated herein by reference), was used in western blot experiments. FIG. 4 shows a silver-stained gel of an untreated $IA^d$ preparation (Lane 1). The same preparation was blotted and stained using 28-16-8S (Lane 2). Comparison of the silver-stained gel and the blot of the untreated sample, Lane 1 with Lane 2, respectively, shows that 28-16-8S recognizes the compact (C) and floppy (F) conformation but not the separate chains, although the relative concentrations of α chain:β chain:compact:floppy were about 1:1.12:1.25:1.37. A western blot of a refolded and reassembled sample is shown in Lane 3. Bands at the positions expected for floppy (F) and compact (C) conformations are seen. This result provides evidence, but does not limit the present invention, that the experiments described herein yield the heterodimeric floppy (F) and compact (C) conformations from separate, unfolded chains.

It is noted that the reduction and reoxidation experiments described above quantitatively release antigenic peptides known to co-purify with MHC molecules, see Demotz, S., et al., *Nature,* 243:682–684 (1989); Wallny, H. J., et al., *Nature* 343:275–278 (1990) (these publications are incorporated herein by reference). As shown in FIG. 1, reassembly is not essential for this purpose. Table I shows that the binding capacity for antigenic peptides is greatly increased after reduction and reoxidation. Although not quantitatively determined, the stoichiometry of antigenic peptide binding to MHC molecules resulting from processes of the present invention may be close to 100%.

What is claimed is:

1. A process for increasing antigen binding capacity of a major histocompatibility complex (MHC) molecule or chain thereof comprising:
   treating an antigen-bound MHC molecule or chain thereof with an effective amount of a reducing agent to release the antigen from the MHC molecule or chain thereof;
   removing the unfolding agent and the released antigen; and
   treating the antigen-free MHC molecule or chain thereof with an effective amount of an oxidizing agent under suitable conditions whereby a functional MHC molecule or chain thereof is produced.

2. A process according to claim 1 wherein the reducing gent is selected from the group consisting of dithiothreitol (DTT), dithioerythritol, and mercaptoethanol.

3. A process according to claim 2 wherein the reducing agent is dithiothreitol (DTT).

4. A process according to claim 3 wherein the effective amount of DTT is in the concentration range from about 1 mM to about 10 mM.

5. A process according to claim 3 further comprising incubating the antigen-bound MHC molecule or chain thereof and DTT for a time period of approximately 1 hour at a temperature of about 37° C.

6. A process according to claim 5 wherein the MHC molecule is a class II molecule in a floppy (F) conformation or a compact (C) conformation or a mixture thereof.

7. A process according to claim 5 wherein the antigen is an autologous peptide.

8. A process for increasing antigen binding capacity of a major histocompatability complex (MHC) molecule or chain thereof comprising:
   treating an antigen-bound MHC molecule or chain thereof with an effective amount of a reducing agent to release the antigen from the MHC molecule or chain thereof;
   removing the reducing agent and the released antigen; and
   treating the antigen-free MHC molecule or chain thereof with an effective amount of a refolding agent selected from the group consisting of $O_2$, $K_3Fe(CN)_6$, and $HgCl_2$, under suitable conditions whereby a functional MHC molecule or chain thereof is produced.

9. A process according to claim 8 wherein the refolding agent is $O_2$ introduced during dialysis in an air-saturated buffer for approximately 12–18 hours.

10. A process for increasing antigen binding capacity of a major histocompatibility complex (MHC) molecule or chain thereof comprising:
    treating an antigen-bound MHC molecule or chain thereof with an effective amount of a reducing agent to release the antigen from the MHC molecule or chain thereof;
    removing the reducing agent and the released antigen;
    treating the antigen-free MHC molecule or chain thereof with an effective amount of an oxidizing agent under suitable conditions whereby a functional MHC molecule or chain thereof is produced; and
    adding a desired antigen to the functional MHC molecule or chain thereof.

11. A process according to claim 10 wherein the reducing agent is dithiothreitol (DTT).

12. A process for separating an antigen from a major histocompatibility complex (MHC) molecule or chain thereof, other than by lowering pH, comprising treating the molecule or chain with an effective amount of a reducing agent.

13. A process according to claim 12 wherein the reducing agent is dithiothreitol (DTT).

* * * * *